(12) United States Patent
Wu et al.

(10) Patent No.: US 10,022,134 B2
(45) Date of Patent: Jul. 17, 2018

(54) ANGLED CRANIOTOME AND MINIMAL PLATING SYSTEM FOR IMPROVED COSMESIS AND STRUCTURAL INTEGRITY OF CRANIOTOMIES

(71) Applicants: Thomas Jefferson University, Philadelphia, PA (US); Thomas Jefferson University Hospital, Inc., Philadelphia, PA (US)

(72) Inventors: Chengyuan Wu, Merion, PA (US); Ashwini D. Sharan, Moorestown, NJ (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 276 days.

(21) Appl. No.: 14/917,135

(22) PCT Filed: Sep. 6, 2014

(86) PCT No.: PCT/US2014/054436
§ 371 (c)(1),
(2) Date: Mar. 7, 2016

(87) PCT Pub. No.: WO2015/035268
PCT Pub. Date: Mar. 12, 2015

(65) Prior Publication Data
US 2016/0192948 A1 Jul. 7, 2016

Related U.S. Application Data

(60) Provisional application No. 61/874,848, filed on Sep. 6, 2013.

(51) Int. Cl.
*A61B 17/16* (2006.01)
*A61B 17/68* (2006.01)

(52) U.S. Cl.
CPC ...... *A61B 17/1695* (2013.01); *A61B 17/1622* (2013.01); *A61B 17/688* (2013.01)

(58) Field of Classification Search
CPC .............. A61B 17/1695; A61B 17/688; A61B 17/1622
See application file for complete search history.

(56) References Cited

U.S. PATENT DOCUMENTS

| 6,506,199 B2 * | 1/2003 | Rogers .............. A61B 17/1695 606/172 |
| 7,740,649 B2 | 6/2010 | Mosca et al. |

(Continued)

FOREIGN PATENT DOCUMENTS

WO 2012153319 A1 11/2012

OTHER PUBLICATIONS

International Search Report issued in International Application No. PCT/US2014/054436, filed Sep. 6, 2013, dated Dec. 22, 2014.

*Primary Examiner* — Christian Sevilla
(74) *Attorney, Agent, or Firm* — Cozen O'Connor

(57) ABSTRACT

In accordance with one embodiment, a device for performing an angled craniotome includes an elongate handle, a footplate, a stem, and an elongate cutting bit. The elongate handle extends in a vertical direction. The footplate is spaced apart from the elongate handle and defines a plane generally perpendicular to the vertical direction. The footplate is offset from the handle in a horizontal direction where the horizontal direction is perpendicular to the vertical direction. The stem has a proximal end and a distal end. The proximal end is coupled to the handle and the distal end is coupled to the footplate. The stem extends from the handle at an oblique angle in the horizontal direction relative to the handle. The elongate cutting bit is coupled to the handle and (Continued)

extends from the handle toward the footplate at the oblique angle in the horizontal direction relative to the handle.

12 Claims, 5 Drawing Sheets

(56) References Cited

U.S. PATENT DOCUMENTS

| | | |
|---|---|---|
| 2002/0143356 A1 | 10/2002 | Rogers et al. |
| 2005/0137598 A1 | 6/2005 | Auth |
| 2006/0178672 A1 | 8/2006 | Shores et al. |
| 2006/0241646 A1 | 10/2006 | Stihl |
| 2012/0191114 A1 | 7/2012 | Packard et al. |

* cited by examiner

ANGLED CRANIOTOME AND MINIMAL PLATING SYSTEM FOR IMPROVED COSMESIS AND STRUCTURAL INTEGRITY OF CRANIOTOMIES

CROSS-REFERENCE TO RELATED APPLICATIONS

This application claims the benefit of U.S. Provisional Patent Application 61/874,848, filed on Sep. 6, 2013, which is hereby incorporated by reference in its entirety.

FIELD OF THE INVENTION

The present invention relates generally to surgical devices for dissecting bone and tissue and, more particularly, to a cutting tool for performing angled cuts therein.

BACKGROUND OF THE INVENTION

A craniotomy involves the surgical removal of a section of bone from the skull to create an opening for accessing and operating on the underlying tissue. When the operation is complete, the removed bone ("bone flap") is placed back within the opening and is reattached to the skull.

Instruments designed to perform the craniotomy are called craniotomes. Craniotomes typically include a cutting bit with a footplate disposed axially perpendicular to the cutting bit. The footplate protects the underlying tissue from contacting the cutting bit when a cut is made perpendicular to the surface of the skull. However, a problem arises when a cut is made at an angle relative to the surface of the skull because the underlying tissue can contact the cutting bit, causing damage to the tissue. Additionally, a perpendicular cut also risks damage to the underlying tissue because the bone flap can become recessed and contact the underlying tissue.

Reattachment of the bone flap is typically accomplished using titanium plates that are placed on the surface of the skull and the surface of the bone flap, spanning the distance therebetween. These plates are affixed to the bone using screws that extend perpendicular to the surface of the skull. These plating systems require a large number of components to be combined to reattach the bone flap. Additionally, current plating systems cause cosmetic defects in the skin overlying the plate because the skin is visibly raised. Further, the plating systems can increase the amount of pain and trauma experienced by the patient, prolong the duration of the surgical procedure, lead to unnecessary and avoidable scarring, erode the overlying skin, increase the risk of infection, and inconvenience the patient with time-consuming return visits to the surgeon to have the fixation means removed.

Thus, it would be desirable to develop a system that overcomes the problems and limitations associated with procedures and devices used in traditional craniotomies.

SUMMARY OF THE INVENTION

In accordance with one embodiment, a device for performing an angled craniotome includes an elongate handle, a footplate, a stem, and an elongate cutting bit. The elongate handle extends in a vertical direction. The footplate is spaced apart from the elongate handle and defines a plane generally perpendicular to the vertical direction. The footplate is offset from the handle in a horizontal direction where the horizontal direction is perpendicular to the vertical direction. The stem has a proximal end and a distal end. The proximal end is coupled to the handle and the distal end is coupled to the footplate. The stem extends from the handle at an oblique angle in the horizontal direction relative to the handle. The elongate cutting bit is coupled to the handle and extends from the handle toward the footplate at the oblique angle in the horizontal direction relative to the handle.

In accordance with another embodiment, a method for performing an angled craniotome includes forming a burr hole through a cranium of a patient, placing the craniotome in the burr hole, engaging an inside of the cranium with a guide surface of the craniotome and cutting an angled channel through the cranium. The craniotome includes an elongate cutting bit defining a first axis, a stem coupled to the cutting bit, and a footplate coupled to the stem. The stem extends generally parallel to the first axis. The footplate includes the guide surface. The engagement of the cranium with the guide surface causes the cutting bit to be disposed at an angle relative to the inside of the cranium.

In accordance with yet another embodiment, a head for being coupled to a handle to perform an angled craniotome includes an elongate cutting bit, a stem coupled to the cutting bit, and a footplate coupled to the stem. The elongate cutting bit defines a first axis. The stem extends generally parallel to the first axis. The footplate extends from the stem in a forward direction at a generally perpendicular angle. The footplate includes a guide surface disposed at an oblique angle relative to the first axis in a horizontal direction. The guide surface is configured to engage an inner surface of a cranium and dispose the cutting bit at the oblique angle relative to the inner surface. The forward direction extends generally from the stem toward the cutting bit and the horizontal direction is perpendicular to the forward direction.

BRIEF DESCRIPTION OF THE DRAWINGS

The invention may best be understood by reference to the following description taken in conjunction with the accompanying drawings.

DETAILED DESCRIPTION OF ILLUSTRATED EMBODIMENTS

Although the invention will be described in connection with certain preferred embodiments, it will be understood that the invention is not limited to those particular embodiments. On the contrary, the invention is intended to cover all alternatives, modifications, and equivalent arrangements as may be included within the spirit and scope of the invention as defined by the appended claims.

Figure 1:
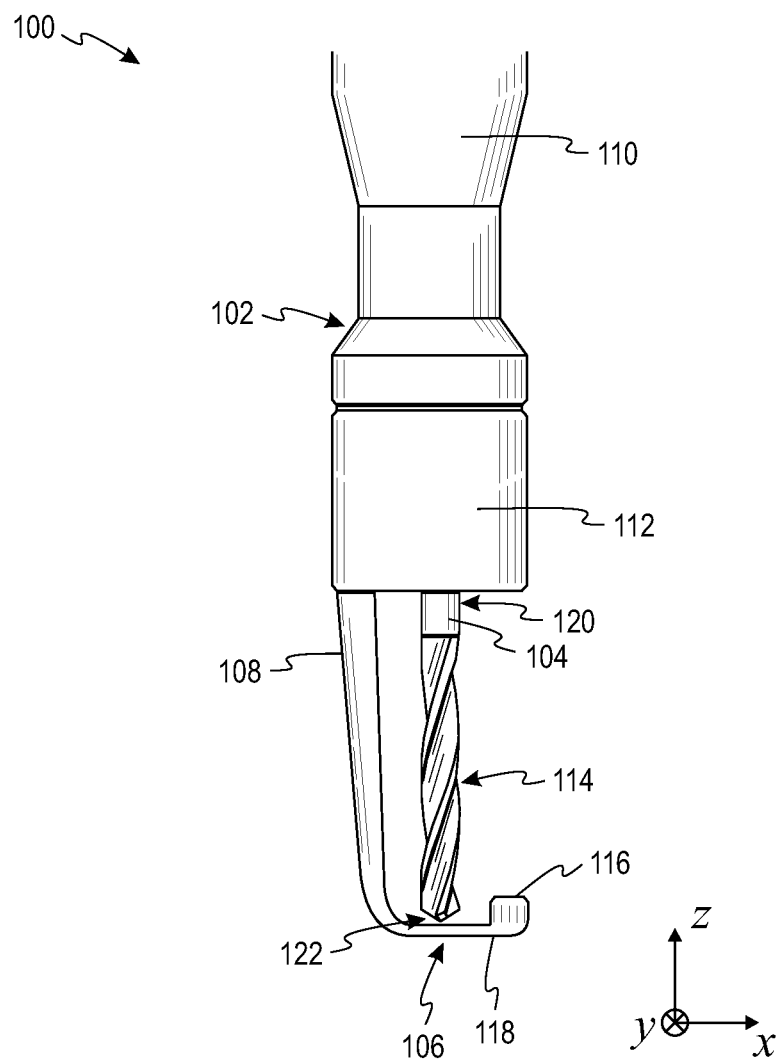
FIG. 1 illustrates a side view of an angled craniotome, according to an embodiment.

Referring now to FIG. 1, a side view of an angled craniotome 100 is shown according to an embodiment. The angled craniotome 100 includes a handle 102, a cutting bit 104, a footplate 106, and a stem 108. The handle 102 has an upper portion 110 and a lower portion 112. The upper portion 110 is configured to be grasped by a surgeon while performing the craniotomy. The lower portion 112 is disposed below the upper portion 110 as viewed when in use and couples the cutting bit 104 to the handle 102.

The cutting bit 104 extends from the handle 102 and includes a cutting surface 114 designed to cut through bone of a patient. The cutting bit 104 has a proximal end 120 nearest the handle 102 and a distal end 122 furthest from handle 102.

Figure 2:
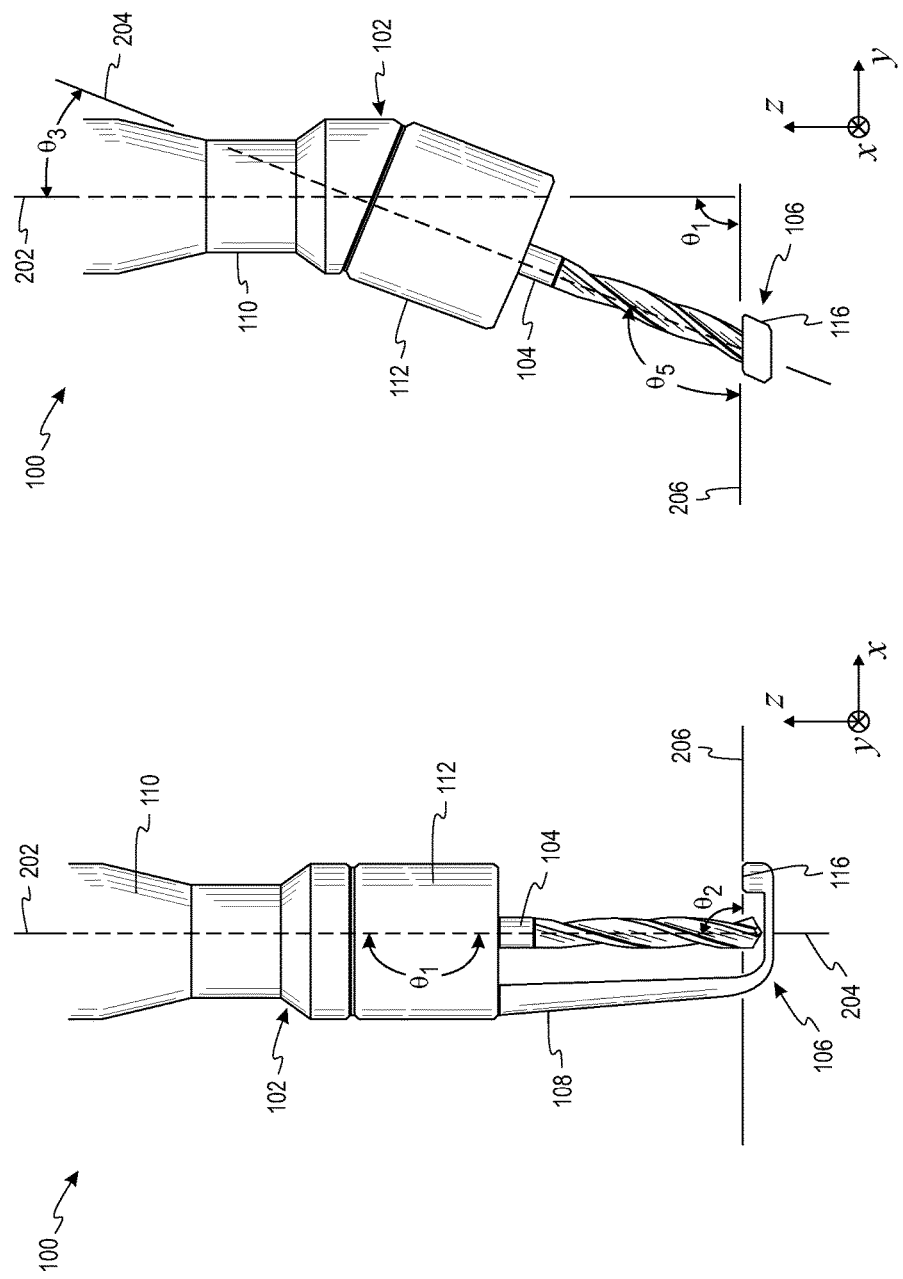
FIG. 2A illustrates a side view of the angled craniotome of FIG. 1.
FIG. 2B illustrates a front view of the angled craniotome of FIG. 1.

The footplate 106 is disposed proximate to the distal end of the cutting bit 104. The footplate 106 includes a guide surface 116 and a protecting surface 118. The guide surface 116 is disposed ahead of the cutting bit 104 in the forward direction and engages the interior surface 308 (FIG. 3) of the cranium. The protecting surface 118 prevents the cutting surface 114 from being exposed to the underlying tissue such as dura 314 (FIG. 3) while the craniotome 100 is in use. For the present disclosure, the forward direction is along the x-axis, the horizontal direction is along the y-axis, and the vertical direction is along the z-axis as illustrated in FIGS. 1, 2A, and 2B.

The stem 108 couples the footplate 106 to the handle 102 and cutting bit 104. The stem 108 is disposed behind the cutting bit 104 such that, when in use, the stem 108 remains in a channel 310 (FIG. 3) cut by the cutting bit 104.

Referring now to FIG. 2A, a side view of the angled craniotome 100 is shown. The upper portion 110 of the handle 102 defines a first axis 202, the cutting bit 104 defines a second axis 204, and the guide surface 116 defines a plane 206. When viewed in the horizontal direction, the first axis 202 and the second axis 204 are disposed at a first angle $\theta_1$ of about 180° relative to each other. Also, when viewed from the horizontal direction, the second axis 204 and the plane 206 are disposed at a second angle $\theta_2$ of about 90° relative to each other.

Referring now to FIG. 2B, a front view of the angled craniotome 100 is shown. When viewed from the front, the first axis 202 and the second axis 204 are disposed at a third angle $\theta_3$ relative to each other. In some aspects, the third angle $\theta_3$ measures between about 20° and about 70°. In further aspects, the third angle $\theta_3$ measures between about 30° and about 60°. In yet further aspects, the third angle $\theta_3$ measures between about 40° and about 50°. Also when viewed from the front, the first axis 202 and the plane 206 are disposed at a fourth angle $\theta_4$ relative to each other. The fourth angle $\theta_4$ measures about 90°. Further, the second axis 204 and the plane 206 are disposed at a fifth angle $\theta_5$ relative to each other. In some aspects, the fifth angle $\theta_5$ measures between about 110° and about 160°. In further aspects, the fifth angle $\theta_5$ measures between about 120° and about 150°. In yet further aspects, the fifth angle $\theta_5$ measures between about 130° and about 140°.

Figure 3:
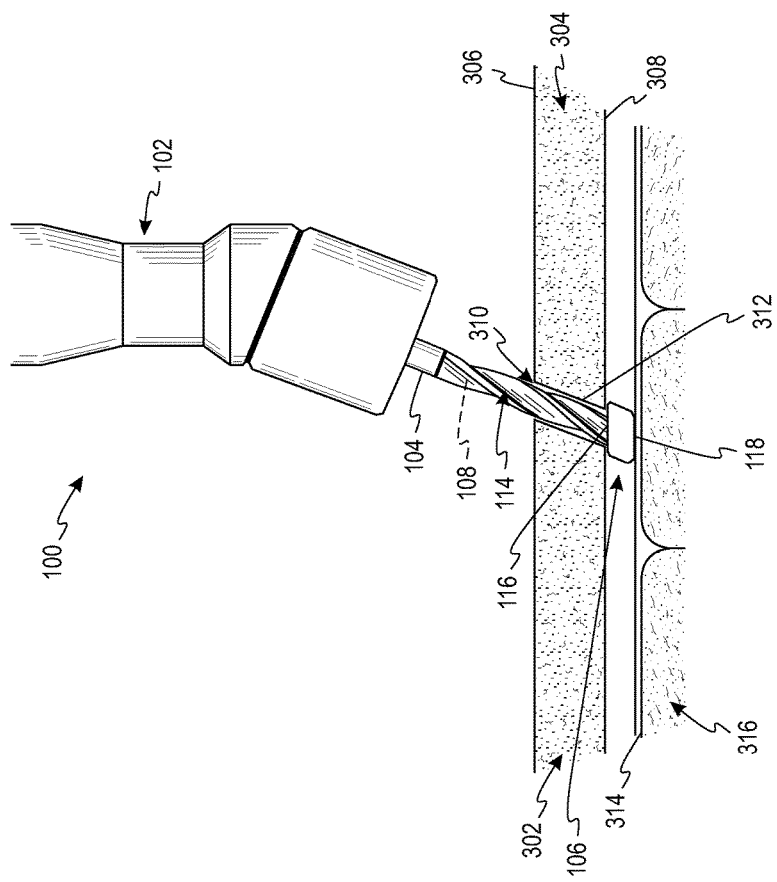
FIG. 3 illustrates a cross-sectional front view of the angled craniotome of FIG. 1 while in use.

FIG. 3 illustrates a cross-sectional front view of the angled craniotome 100 while in use. To begin removal of a bone flap 302 from a patient's skull 304, a burr hole is cut in the skull 304. The burr hole is of sufficient size to receive the cutting bit 104, footplate 106, and the stem 108 of the craniotome 100. In some aspects, the burr hole has a diameter of about 8 mm to about 16 mm. In further aspects, the burr hole has a diameter of about 10 mm to about 14 mm. In some aspects, the burr hole is generally perpendicular to the outer surface 306 of the skull 304 and extends to the inner surface 308. In some aspects, the burr hole extends from the outer surface 306 of the skull 304 toward the inner surface 308 at the fifth angle $\theta_5$ with the opening at the outer surface 306 disposed further from the center of the bone flap 302 than the opening on the inner surface 308.

The craniotome 100 is inserted through the burr hole until the footplate 106 is disposed below the inner surface 308. After insertion through the burr hole, the craniotome 100 is moved forward (in the positive x-direction of FIGS. 1 and 2) such that the cutting surface 114 contacts the skull 304. Engagement of the cutting surface 114 with the skull 304 results in the angled craniotome 100 cutting the channel 310 through the skull 304. The resulting channel 310 includes beveled edges 312. The beveled edges 312 taper toward the center of the bone flap 302 such that the bone flap 302 can be removed from the skull 304, but cannot become recessed. This provides increased safety for the craniotomy by lowering the risk of the bone flap 302 damaging the underlying tissue, such as the dura 314 and brain tissue 316, and additionally improves the cosmesis of the craniotomy.

During cutting, the footplate 106 is disposed between the inner surface 308 of the skull 304 and the dura 314 as shown in FIG. 3. The guide surface 116 engages the inner surface 308 and aids in the maintaining the cutting bit 104 at the fifth angle $\theta_5$ to cut the angled channel 310. The protecting surface 118 remains between the dura 314 and any portion of the cutting surface 114 that might otherwise damage the dura 314 and/or the brain 316.

Figure 4:
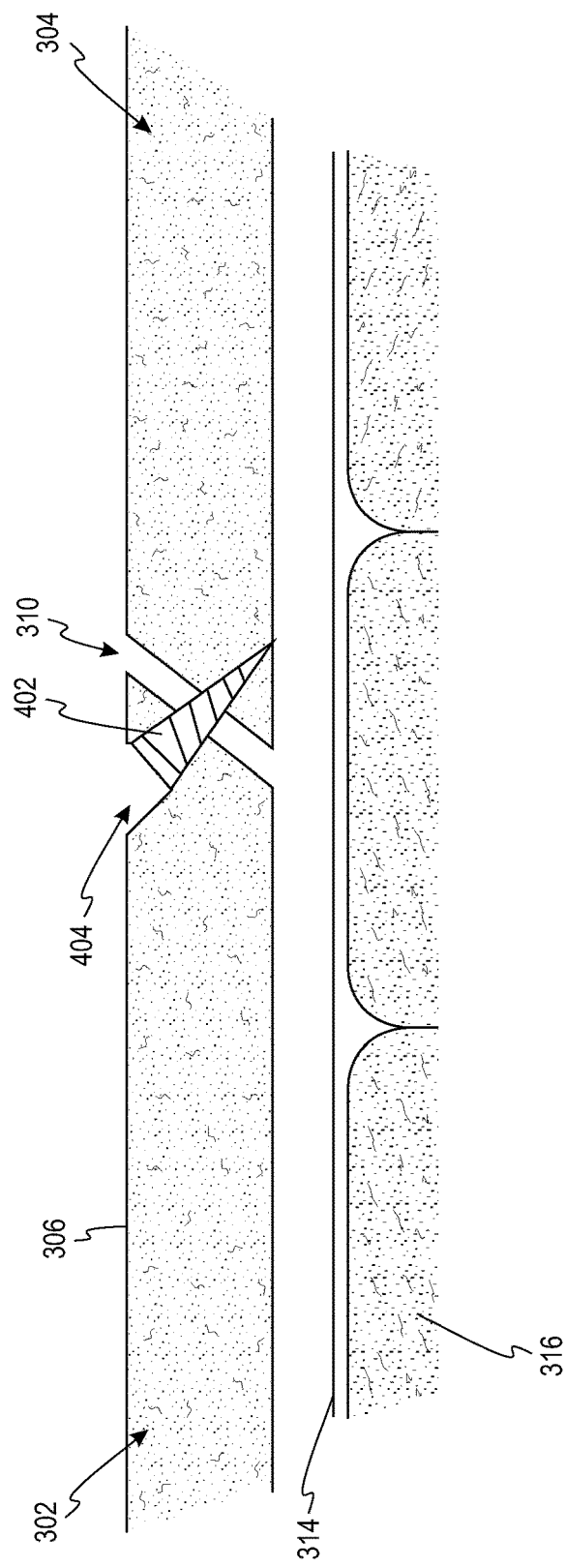
FIG. 4 illustrates a minimal plating system, according to an embodiment.

Referring now to FIG. 4, a minimal plating system is illustrated according to an embodiment. The minimal plating system includes a fastener 402 disposed within a pilot hole 404. The fastener 402 can be, for example, a screw or pin. Engagement of the fastener 402 with the bone flap 302 and the skull 304 prevents the bone flap 302 from being rotated and/or removed. Inward movement of the bone flap 302 is inhibited by both the fastener 402 and the shape of the channel 310. In some aspects, the beveled edge of the bone flap 302 is in contact with the skull 304. In other aspects, at least a portion of the channel 310 is filled with an adhesive or other material to replace the bone that was removed by the cutting bit 104.

The pilot hole 404 begins on an outer surface of the bone flap 302 and extends at least partway therethrough in the direction of the skull 304. In some aspects, the pilot hole 404 extends at an angle that is approximately perpendicular to the angle of the channel 310. In some aspects, the pilot hole 404 also extends through a portion of the skull 304. The pilot hole 404 can be formed using a variety of different tools including a drill or an awl. The pilot hole 404 prevents or inhibits the fastener 402 from fracturing the bone flap 302. It is contemplated that specialized fasteners 402 can be used that include, for example, a cutting edge that prevents or inhibits fracturing of the bone flap 302 and/or skull 304. The fastener 402 may configured to be mounted flush with the outer surface 306 of the bone flap 302 as shown or may be countersunk into the bone flap 302.

In some aspects, the fastener 402 and/or the recess formed by pilot hole 404 include a specialized cap or other marker to facilitate identification for a revision craniotomy. For example, in some aspects, a cap is fitted within the pilot hole 404 to serve as a visual marker. Additionally or alternatively, fiducial markers may be used to identify the location of the bone flap and fasteners. The surgeon can then use an imaging device to identify the fiducial markers with or without any visual indication on the skin or scalp of the patient.

Patient satisfaction can be increased using the minimal plating system because the cosmetic appearance of the craniotomy site is increased. Specifically, the minimal plating system does not cause the noticeably raised and abnormal areas created by typical plating systems. Additionally, the use of caps that are visible to the surgeon is more favorable than typical plating systems because the caps can be designed to provide little or no cosmetic disturbance. Moreover, minimal plating may reduce wound infections by lowering the risk of skin erosion and reducing foreign bodies remaining after reattachment because less hardware is needed. Additionally, the hardware itself includes fewer components, further lowering the likelihood of an infection. Further, the minimal plating system lowers discomfort of the patient and also reduces the risk of splitting the patient's skin when an object contacts the skin covering the craniotomy site.

Figure 5:
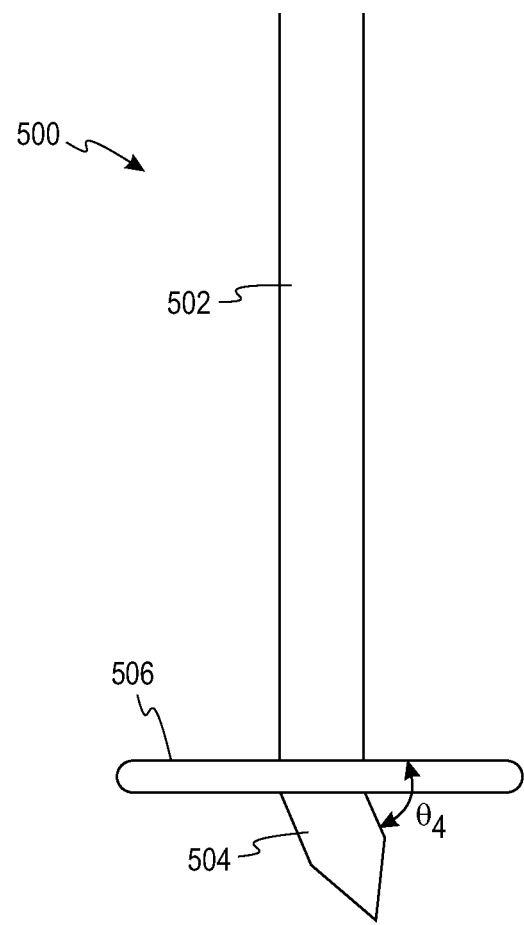
FIG. 5 illustrates a side view of an awl for use with the minimal plating system, according to an embodiment.

Referring now to FIG. 5, an awl 500 for use with the minimal plating system is shown according to an embodiment. The awl 500 includes a shaft 502, a tip 504, and a flange 506. The flange 506 controls the maximum penetration of the tip 504. In the illustrated embodiment, the flange 506 is oriented generally perpendicular to the shaft 502. In some aspects, the tip 504 extends coaxially from the shaft 502 and the flange 506 is disposed at the angle $\theta_A$ relative to both the shaft 502 and the tip 504.

The tip 504 is at an angle $\theta_A$ relative to the flange 506. In the illustrated embodiment, the angle $\theta_A$ is selected to allow the awl to create a pilot hole 404 that is generally perpendicular to the channel 310. Thus, in some aspects, the angle $\theta_A$ is between about 20° and about 70°. In further aspects, the angle $\theta_A$ measures between about 30° and about 60°. In yet further aspects, the angle $\theta_A$ measures between about 40° and about 50°. In some aspects, the measure of angle $\theta_A$ is about the measure of the third angle $\theta_3$. It is contemplated that the measure of angle $\theta_A$ can be different from the measure of the third angle $\theta_3$ so that the pilot hole 404 is at an oblique angle to the channel 310.

When using the awl 500, the surgeon places the tip 504 against the bone flap 302 with the shaft 502 oriented generally perpendicular to the outer surface 306. The surgeon then drives the tip 504 into the bone flap 302 by impacting the shaft 502 with an object. The tip 504 penetrates until reaching a predetermined depth. The predetermined depth is set by the flange 506 contacting the outer surface 306 of the bone flap 302. The predetermined depth can be, for example, a portion of the way through the bone flap 302, to the channel 310, or a portion of the way through the skull 304.

In some aspects, the flange 506 is slidably disposed on the shaft 502. When in use, the surgeon places the flange 506 against the outer surface 306 of the bone flap 302. The flange 506 holds the tip 504 at the desired angle. The surgeon then drives the tip 504 into the bone flap 302 by impacting the shaft 502 with an object. The shaft 502 slides through the flange 506 until the flange 506 contacts a stop point on the shaft 502 when the tip 504 reaches a predetermined depth. The stop point can include the shaft 502 being a different shape, having a protrusion, etc.

In some aspects, a kit of components is provided having at least two heads for being removably coupled to a standard craniotome handle. Each head includes a cutting bit, footplate, and stem. The first head of the at least two heads is configured to cut in a first direction (e.g., clockwise) and the second head is configured to cut in a second direction (e.g., counter-clockwise). When the first head is coupled to the handle, the cutting bit extends at a first angle relative to the handle in the horizontal direction. In some aspects, the first angle measures between about 20° and about 70° from vertical in a first direction. The stem extends from the handle at generally the first angle such that the stem follows the cutting bit through the channel when the craniotome is in use. The footplate is oriented at a second angle relative to the cutting bit in the horizontal direction. In some aspects, the second angle is complementary to the first angle, or between about 70° and about 20°.

When the second head is coupled to the handle, the cutting bit extends at a third angle relative to the handle in the horizontal direction. In some aspects, the third angle measures between about 20° and about 70° from vertical in a second direction, opposite the first direction. The stem extends from the handle at generally the third angle such that the stem follows the cutting bit through the channel when the craniotome is in use. The footplate is oriented at a fourth angle relative to the cutting bit in the horizontal direction. In some aspects, the fourth angle is complementary to the fourth angle, or between about 70° and about 20°.

In some aspects, the angle of the cutting bit relative to the handle is adjustable by a surgeon. This can be accomplished, for example, using an articulating head coupled to the handle. The articulating head can move through a range of desired angles such as between 20° and between 70° from vertical. The articulating head can then be secured at a single angle so that angle of the channel remains constant during the desired portion of the craniotomy.

In some aspects, the angle of the footplate relative to the cutting bit is adjustable by a surgeon. This can be accomplished, for example, using an articulating footplate that rolls about the x-axis. The plane of the articulating footplate can move through a range of desired angles such as between about 20° and between about 70° from the axis of the cutting bit. The articulating footplate can then be secured at a single angle so that angle of the channel remains constant during the desired portion of the craniotome. The securing can be accomplished through known means such as pinning or a frictional/compression fitting that holds the footplate relative to the stem.

In some aspects, a kit of components includes an awl and a plurality of screws. The awl is configured to create a pilot hole at a predetermined angle. Each of the plurality of screws is sized according to the diameter of the pilot hole. Additionally, the length of each of the plurality of screws is determined by the angle of the awl. The shallower the angle of the awl, the longer the screw may be without penetrating the inner surface of the skull and risking damage to the underlying tissue. In some aspects, the screws are between about 4 mm and about 10 mm in length. In further aspects, the screws are between about 6 mm and about 9 mm in length. In yet further aspects, the screws are between about 7 mm and about 8 mm in length.

It is contemplated that the craniotome, the awl, and/or components thereof can be disposable. For example, in some aspects, the cutting bit is disposable. In some aspects, the stem and footplate are disposable. In in further aspects, the lower portion of the handle is disposable.

It will be evident to those skilled in the art that the invention is not limited to the details of the foregoing illustrated embodiment and that the present invention may be embodied in other specific forms without departing from the spirit or essential attributes thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A device for performing an angled craniotomy comprising:
   an elongate handle extending in a vertical direction;
   a footplate spaced apart from the elongate handle and defining a plane generally perpendicular to the vertical direction, the footplate being offset from the handle in a horizontal direction, the horizontal direction being perpendicular to the vertical direction;
   a stem having a proximal end and a distal end, the proximal end coupled to the handle and the distal end coupled to the footplate, the stem extending from the handle at an oblique angle in the horizontal direction relative to the handle; and
   an elongate cutting bit coupled to the handle and extending from the handle toward the footplate at the oblique angle in the horizontal direction relative to the handle.

2. The device of claim 1, wherein the oblique angle is between about 20 degrees and about 70 degrees.

3. The device of claim 1, wherein the oblique angle is between about 40 degrees and about 50 degrees.

4. The device of claim 1, further comprising a head removably coupled to the handle, the head including the cutting bit, the stem, and the footplate.

5. The device of claim 1, wherein the footplate is adjustable such that a surgeon may select the oblique angle between about 20 degrees and about 70 degrees.

6. A head for being coupled to a handle to perform an angled craniotomy, the head comprising:
   an elongate cutting bit defining a first axis;
   a stem coupled to the cutting bit, the stem extending generally parallel to the first axis; and
   a footplate coupled to the stem and extending from the stem in a forward direction at a generally perpendicular angle, the footplate including a guide surface disposed at an oblique angle relative to the first axis in a horizontal direction, the guide surface configured to engage an inner surface of a cranium and dispose the cutting bit at the oblique angle relative to the inner surface,
   wherein the forward direction extends generally from the stem toward the cutting bit and the horizontal direction is perpendicular to the forward direction.

7. The head of claim 6, wherein the oblique angle is between about 20 degrees and about 70 degrees.

8. The head of claim 6, wherein the oblique angle is between about 40 degrees and about 50 degrees.

9. The head of claim 6, further comprising an elongate handle coupled to the stem and the cutting bit, the handle defining a second axis disposed generally perpendicular to the guide surface.

10. The head of claim 6, wherein the cutting bit and the stem are removably coupled to a handle.

11. The head of claim 6, wherein the oblique angle is at least one of adjustable from about 20 degrees or adjustable up to about 70 degrees.

12. The head of claim 6, wherein the footplate prevents a dura of a patient from contacting a portion of the cutting bit when in use.

* * * * *